United States Patent [19]
Virno et al.

[11] Patent Number: 5,227,404
[45] Date of Patent: Jul. 13, 1993

[54] PHARMACEUTICAL COMPOSITION FOR THE TREATMENT OF GLAUCOMATOUS OPTIC NEUROPATHY

[75] Inventors: Michele Virno, Rome; Annibale Gazzaniga, Rescaldina, both of Italy

[73] Assignee: Zambon Group S.p.A., Vicenza, Italy

[21] Appl. No.: 866,415

[22] Filed: Apr. 10, 1992

[30] Foreign Application Priority Data

Apr. 19, 1991 [IT] Italy .................. MI91 A 001095

[51] Int. Cl.$^5$ ........................... A61K 31/225
[52] U.S. Cl. ........................... 514/547; 514/912; 514/913
[58] Field of Search ............... 514/547, 912, 913

[56] References Cited

U.S. PATENT DOCUMENTS 4,764,530  8/1988  Carenzi et al. .

FOREIGN PATENT DOCUMENTS 0393782 10/1990 European Pat. Off. .
3514508 10/1986 Fed. Rep. of Germany .
8603970  7/1986 World Int. Prop. O. .

OTHER PUBLICATIONS

Chemical Abstracts, vol. 114, No. 23, Jun. 10, 1991, Abstract 228543n, (and EP-A-393 782).
International Opthamology, vol. 13, 1989, pp. 109–112, Kluwer Academic Publishers, (NL) J. P. Giraldi et al.
Boll Ocul 66 (5), 1987. 833–846. Virno et al.

Primary Examiner—Frederick E. Waddell
Assistant Examiner—Zohreh A. Fay
Attorney, Agent, or Firm—Stevens, Davis, Miller & Mosher

[57] ABSTRACT

A pharmaceutical composition for the treatment of glaucomatous optic neuropathy comprising the 4-[2-(methyl-amino)-ethyl]-1,2-phenylene ester of 2-methyl-propanoic acid (Ibopamine) or a pharmaceutically acceptable acid addition salt thereof are described.

3 Claims, No Drawings

PHARMACEUTICAL COMPOSITION FOR THE TREATMENT OF GLAUCOMATOUS OPTIC NEUROPATHY

DESCRIPTION

This invention relates to a pharmaceutical composition for the treatment of glaucomatous optic neuropathy and, more particularly, to a pharmaceutical composition for the treatment of glaucomatous optic neuropathy by oral route comprising the 4-[2-(methyl-amino)-ethyl]-1,2-phenylene ester of 2-methyl propanoic acid or a pharmaceutically acceptable acid addition salt thereof.

The 4-[2-(methyl-amino)-ethyl]-1,2-phenylene ester of 2-methylpropanoic acid is a well known cardiovascular drug whose international non-proprietary name (INN) is Ibopamine (Merck Index, XI Ed., No. 4807, p. 775).

In cardiovascular therapy Ibopamine is administered systemically and, in particular, orally, usually in the form of hydrochloride salt.

It is also known that Ibopamine may be used in ophthalmology to induce mydriasis after topical administration (European Patent No. 0205606-SIMES Societá Italiana Medicinali e Sintetici S.p.A.).

The concomitant systemic treatment of glaucomatous optic neuropathy and local treatment of ocular hypertension have been recently suggested [Pecori Giraldi J. et al. Atti Soc. Oftalm. Lombarda, 42, p. 519, (1987) e Virno M. et al., International Ophthalmology, 13, p. 109, (1989)].

Such treatments make use of neurotrophic drugs such as gangliosides (Merck Index, XI Ed. No. 4264, p. 683) and citicoline (Merck Index, XI Ed., No. 2321, p. 361) and in some cases satisfactory results have been obtained.

However, treatment with these neurotrophic drugs necessarily implies a parenteral route of administration, for instance intramuscularly, which generally does not meet with the patients' compliance while said compliance is so much more important the longer the therapy is, such as in the case of treatment of glaucomatous optic neuropathy.

Therefore, a drug is still in great demand capable of treating glaucomatous optic neuropathy by oral route.

Now it has been found that the oral administration of Ibopamine and of pharmaceutically acceptable acid addition salts thereof improves the sensitivity of the retina in subjects affected by glaucomatous optic neuropathy.

It is therefore an object of this invention to provide a pharmaceutical composition for the treatment of glaucomatous optic neuropathy by oral route comprising an effective amount of Ibopamine or a pharmaceutically acceptable acid addition salt thereof, together with at least a pharmaceutically acceptable inert ingredient.

A further object of this invention is to provide a method of treatment comprising administering to a patient affected by glaucomatous optic neuropathy an effective amount of Ibopamine or a pharmaceutically acceptable acid addition salt thereof.

The pharmaceutical compositions of this invention can be in solid form as tablets, pills, granules, coated tables, capsules and slow release forms, or in liquid form as solutions or suspensions.

In addition to the usual carriers, the compositions of this invention may contain additives suitable for pharmaceutical use as preservatives, stabilizers, or flavouring and colouring agents.

The pharmaceutical compositions can be made according to conventional techniques of the pharmaceutical chemist involving mixing, granulating and compressing when necessary, or variously mixing and dissolving the ingredients as appropriate to give the desired end product.

The efficacy of Ibopamine in the treatment of glaucomatous optic neuropathy has been proved in vivo by means of the visual field test and by the evaluation of the variations in the sensitivity of the retina after oral administration at different dosages for a prolonged period of time.

The methods used for the visual field test are both the Humphrey automatic perimeter and the Video-screen Computerized Perimeter (V.C.P.).

Both methods are widely described in the literature; just as an example we will cite Heijl A., The Humphrey field analyzer, construction and concepts., Doc. Ophthalmology, 102, 40, (1984).

The experiments have been carried out on subjects undergoing concomitantly antihypertensive local therapy.

Oral administration of Ibopamine proved to be effective in improving the sensitivity of the retina in subjects affected by glaucomatous optic neuropathy.

Improvement of the sensitivity of the retina is also associated with the reduction in the fluctuation of the sensitivity of the retina itself. In other words, Ibopamine is capable of improving the sensitivity of the retina and to prevent further worsening of the visual field defects. Therefore Ibopamine is also effective in preventing, in subjects affected by ocular hypertension, the incipience of glaucomatous optic neuropathy.

Furthermore, no evidence of undesirable side effects has been found. More particularly, no cases of increase in ocular pression or modifications in the diameter of the pupils have been observed.

. It is also important to notice that Ibopamine is active in the treatment of glaucomatous optic neuropathy by oral administration even at low doses.

In fact, therapeutic doses are generally of from 100 to 400 mg per day, and preferably of from 150 to 300 mg per day subdivided in several repeated doses.

For the purpose of better illustrating the present invention the following examples are now given.

EXAMPLE 1

Eight subjects, for a total of 15 eyes, with marked alterations of the ocular perimeter, have been selected.

5 of these subjects had glaucoma, 2 had a high degree of myopia and 1 was affected by senile macular degeneration.

The treatment has been performed out by administering Ibopamine orally at a dosage of 50 mg/3 times a day for 15 consecutive days.

The visual field control has been performed according to the V.C.P. method.

All subjects had already been instructed in the execution of the test and therefore the influence of the learning effect on the answers obtained can be excluded.

The variations in the sensitivity of the retina in a 50 year old female subject are shown in the following table.

TABLE 1

Results obtained with V.C.P. before and after treatment with Ibopamine 50 mg/3 times a day for 15 days.
C.L., female, 50 years old, glaucomatous optic neuropathy in a myopic patient.

|  | Total Area (mm²) | Level 1 | Level 2 | Level 3 | Level 4 | Level 5 | Level 6 |
|---|---|---|---|---|---|---|---|
| Before treatment | 13604 | 14 | 277 | 358 | 169 | 65 | 77 |
| After treatment | 9620 | 67 | 420 | 267 | 118 | 48 | 40 |

The data of Table 1 show a manifest improvement in the sensitivity of the retina after treatment with Ibopamine.

In fact, the treated subject has shown a reduction in the total scotomatosous area and an increased perception of the points of level 1 and 2 (corresponding to the highest sensitivity of the retina) with reduction of those of higher surface (levels 4, 5 and 6).

Table 2 show the overall data, referred to the total number of treated subjects, obtained with V.C.P. and by applying the Student's t-test for the statistical analysis.

TABLE 2

Average values of the results obtained with V.C.P. before and after treatment with Ibopamine 50 mg/3 times a day for 15 days on 8 healthy subjects (5 had glaucoma, 2 had a high degree of myopia, 1 was affected by macular senile degeneration). Values between brackets indicate the standard deviation.

|  | Total Area (mm²) | Level 1 | Level 2 | Level 3 | Level 4 | Level 5 | Level 6 |
|---|---|---|---|---|---|---|---|
| Before treatment | 19401 (18882) | 158 (229) | 273 (207) | 181 (164) | 102 (103) | 86 (94) | 117 (206) |
| After treatment | 16167 (15904) | 245 (348) | 262 (245) | 154 (138) | 100 (106) | 97 (117) | 113 (149) |
| Paired t-test | 3.92 | 2.48 | 0.42 | 1.00 | 0.30 | 0.78 | 2.80 |
| "two-tailed" p | 0.0015 | 0.02 | 0.60 | 0.20 | 0.70 | 0.40 | 0.012 |

The most significant data of the statistical analysis turned out to be the reduction in the total scotomatosous area the increased perception of the points of level 1 and the reduction of those of level 6.

These results show how Ibopamine is active in increasing the sensitivity of the retina in patients affected by glaucomatous optic neuropathy.

EXAMPLE 2

Twelve patients with glaucoma, for a total of 20 eyes, with marked alterations of the ocular perimeter, have been selected.

The treatment has been carried out by administering Ibopamine orally at a dosage of 100 mg/3 times a day for 15 consecutive days.

The visual field control has been performed according to the method of the Humphrey automatic perimeter.

All subjects were already instructed in the execution of the test and therefore the influence of the learning effect on the answers obtained can be excluded.

TABLE 3

Results obtained according to the Humphrey automatic perimeter before and after treatment with Ibopamine 100 mg/3 times a day for 15 days.

| Overall indices | Before treatment | After treatment |
|---|---|---|
| S.V., female, 52 years old, right eye, glaucomatous optic neuropathy in a myopic patient with Fuch's central spot. | | |
| Mean defect (M.D.) | −11.90 | −7.37 |
| Possible size of damage (P.S.D.) | 5.16 | 3.80 |
| Short-term threshold fluctuation (S.F.) | 3.19 | 1.70 |
| Corrected possible size of damage (C.P.S.D.) | 3.68 | 3.27 |
| C.L., male, 60 years old, right eye, glaucomatous optic neuropathy | | |
| Mean defect (M.D.) | −12.26 | −8.41 |
| Possible size of damage (P.S.D.) | 12.87 | 7.88 |
| Short-term threshold fluctuation (S.F.) | 2.48 | 1.07 |
| Corrected possible size of damage (C.P.S.D.) | 12.58 | 7.90 |
| C.L., male, 60 years old, left eye, glaucomatous optic neuropathy | | |
| Mean defect (M.D.) | −10.89 | −9.51 |
| Possible size of damage (P.S.D.) | 12.06 | 7.20 |
| Short-term threshold fluctuation (S.F.) | 3.66 | 1.72 |
| Corrected possible size of damage (C.P.S.D.) | 11.32 | 6.33 |
| F.S.[a], male, 68 years old, right eye, very advanced glaucomatous optic neuropathy | | |
| Mean defect (M.D.) | −27.54 | −18.02 |
| Possible size of damage (P.S.D.) | 8.83 | 8.35 |
| Short-term threshold fluctuation (S.F.) | 7.34 | 2.98 |
| Corrected possible size of damage (C.P.S.D.) | — | 7.63 |
| P.M., female, 65 years old, right eye, glaucomatous optic neuropathy | | |
| Mean defect (M.D.) | −17.58 | −15.88 |
| Possible size of damage (P.S.D.) | 10.45 | 10.34 |
| Short-term threshold fluctuation (S.F.) | 2.84 | 2.33 |
| Corrected possible size of damage (C.P.S.D.) | 9.94 | 3.77 |

[a] The improvement obtained after 15 days of treatment has been maintained for over a month when therapy with Ibopamine is pursued.

The following Table 4 show the overall data referred to the total number of subjects treated, obtained with the Humphrey automatic perimeter and by applying the Student's t-test for the statistical analysis.

TABLE 4

Average values obtained with the Humphrey automatic perimeter before and after treatment of 12 subjects affected by glaucoma, with Ibopamine 100 mg/3 times a day for 15 days. Values between brackets indicate the standard deviation.

|  | Mean Defect (M.D.) | Possible Size Damage (P.S.D.) | Short-term Threshold Fluctuation (S.F.) | Corrected Possible Damage (C.P.S.D.) |
|---|---|---|---|---|
| Before treatment | 11.06 (9.32) | 5.82 (3.91) | 2.58 (1.72) | 4.75 (4.14) |
| After treatment | 10.13 (8.26) | 5.75 (3.21) | 1.81 (0.76) | 5.27 (3.28) |
| Paired t-test | 2.17 | 0.18 | 2.13 | 1.01 |
| "two-tailed" p | 0.044 | 0.85 | 0.047 | 0.32 |

The data obtained with the Humphrey automatic perimeter method show how Ibopamine has improved the sensitivity of the retina in the treated subjects. In particular, the most significant data in the statistical analysis have turned out to be the improvement of the values of the mean defect (M.D.) and of the short-term threshold fluctuation (S.F.).

This improvement indicates that Ibopamine both improves the sensitivity of the retina in toto and, by reducing the fluctuation, stabilizes the same, thus preventing the evolution of the visual field defects.

We claim:

1. A method for the treatment of a patient affected by glaucomatous optic neuropathy, said method consisting in administering to the patient by the oral route a therapeutically effective amount of Ibopamine or a pharmaceutically acceptable acid addition salt thereof.

2. A method of treatment according to claim 1, wherein the effective amount of Ibopamine is of from 100 to 400 mg per day.

3. A method of treatment according to claim 1, wherein the effective amount of Ibopamine is of from 150 to 300 mg per day.

* * * * *